US009149062B2

(12) United States Patent
Friesen et al.

(10) Patent No.: US 9,149,062 B2
(45) Date of Patent: Oct. 6, 2015

(54) METHODS AND COMPOSITIONS FOR THE PREVENTION AND TREATMENT OF KIDNEY DISEASE

(75) Inventors: Kim Gene Friesen, Carthage, IN (US); Ryan Michael Yamka, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1079 days.

(21) Appl. No.: 11/994,342

(22) PCT Filed: Jun. 29, 2006

(86) PCT No.: PCT/US2006/025394
§ 371 (c)(1),
(2), (4) Date: Jul. 21, 2008

(87) PCT Pub. No.: WO2007/002836
PCT Pub. Date: Jan. 4, 2007

(65) Prior Publication Data
US 2009/0197804 A1   Aug. 6, 2009

Related U.S. Application Data

(60) Provisional application No. 60/695,152, filed on Jun. 29, 2005.

(51) Int. Cl.
| A23J 1/02 | (2006.01) |
| A23K 1/18 | (2006.01) |
| A23B 4/00 | (2006.01) |
| A23L 1/304 | (2006.01) |
| A23K 1/175 | (2006.01) |
| A23L 1/29 | (2006.01) |
| A23L 1/305 | (2006.01) |

(52) U.S. Cl.
CPC ............ *A23L 1/304* (2013.01); *A23K 1/175* (2013.01); *A23K 1/1846* (2013.01); *A23L 1/296* (2013.01); *A23L 1/305* (2013.01)

(58) Field of Classification Search
None
See application file for complete search history.

(56) References Cited

U.S. PATENT DOCUMENTS

| 5,339,771 | A |   | 8/1994 | Axelrod |         |
| 5,419,283 | A |   | 5/1995 | Leo |         |
| 5,723,441 | A |   | 3/1998 | Higley et al. |         |
| 6,039,952 | A |   | 3/2000 | Sunvold et al. |         |
| 6,447,989 | B1 |   | 9/2002 | Comper |         |
| 6,458,767 | B1 |   | 10/2002 | Murphy-Ullrich et al. |         |
| 6,477,989 | B2 |   | 11/2002 | Suzuki et al. |         |
| 6,482,448 | B2 | * | 11/2002 | Tabor | 424/757 |
| 6,492,325 | B1 |   | 12/2002 | Cosgrove |         |
| 6,521,647 | B2 | * | 2/2003 | Foster | 514/356 |
| 6,589,748 | B2 |   | 7/2003 | Comper |         |
| 6,599,876 | B2 |   | 7/2003 | Kojima |         |
| 6,784,159 | B2 |   | 8/2004 | Holub et al. |         |
| 6,946,488 | B2 | * | 9/2005 | Hayek et al. | 514/558 |
| 8,501,223 | B2 | * | 8/2013 | Wedekind et al. | 424/442 |
| 8,633,246 | B2 | * | 1/2014 | Fritsch et al. | 514/560 |
| 2001/0043983 | A1 | * | 11/2001 | Hamilton | 426/635 |
| 2002/0028762 | A1 |   | 3/2002 | Kojima |         |
| 2005/0026225 | A1 |   | 2/2005 | Comper |         |
| 2005/0064017 | A1 |   | 3/2005 | Bierer |         |
| 2005/0123543 | A1 |   | 6/2005 | Kretzier et al. |         |

FOREIGN PATENT DOCUMENTS

| CN | 2540937 Y | 3/2003 |
| JP | H06-197715 | 7/1994 |
| JP | 2009-500017 A | 1/2009 |
| WO | WO 00/65584 | 11/2000 |
| WO | 0149130 A | 7/2001 |
| WO | WO2004/113570 | 12/2004 |

OTHER PUBLICATIONS

Diet-Chronic Kidney Disease 2003. http://health.allrefer.com/health/diet-chronic-kidney-disease-info.html, downloaded May 14, 2010).*
Agricultural Factbook 2001-2002, chapter 2, www.usda.gov/factbood/chapter2.htm, downloaded Aug. 11, 2010.*
Pion et al. 1987. Science 237:764.*
AAFCO Cat Food Nutrient Profiles 2003 (see http://maxshouse.com/nutrition/aafco_cat_food_nutrient_profiles.htm, downloaded Jul. 10, 2014.*
Straus, "Diet & Supplements for Dogs with Kidney Disease" Mar. 28, 2005 http://web.archive.org/web/20050403081003/http://www.dogaware.com/kidney.html.
University of Utah Health Sciences Center, Diet for Kidney Disease (1998) http://web.archive.org/web20050124154407/http://uuhsc.utah.edu/pated/handouts/handout.cfm?id=858 Utah.
International Search Report Dated Jun. 3, 2008.
Abstract of Japan JP11243879(A) Sep. 14, 1999.
Abstract of Japan JP2002204668(A) Jul. 23, 2002.
Abstract of Japan JP2003334009(A) Nov. 25, 2003.
European Search Report P6774283.3-2114/1896070 Mailed Apr. 1, 2009.
Anonymous: "Ami Products—Ingredients" Internet Citation, [Online] XP002446899 Retrieved from the Internet: URL:http://ami.aminews.net/en_ingredient1.html. [retrieved on Aug. 14, 2007].
Pedrini MT, Levey AS, Lau J. Chalmers TC, Wang PH. The effect of dietary protein restriction on the progression of diabetic and nondiebetic renal diseases: a meta-analysis. Ann Inter Med 1996; 124:627-32.
Klhar S. Levey AS, Beck GJ, Caggiula AW, Hunsicker L, Kusek JW, et al.The effects of dietary protein restriction and blood-pressure control on the progression of chronic renal disease. Modification of Diet in Renal Disease Study Group. N Engl J Med. 1994;330:877-94.
American Feed Control Officials, Inc., Official publication, pp. 129-137 (2004).
Journal of Japanese Society of Pathological State Nutrition, Nihon Byoutai Eiyougakkai shi, 6(1) p. 67-74 (2003). English translation of relevent portions provided.

(Continued)

Primary Examiner — Shulamith H Shafer

(57) ABSTRACT

Compositions for preventing or treating kidney disease comprising one or more food ingredients containing relatively low amounts of protein, sodium, and potassium, typically protein in amounts of from about 5% to about 40%, sodium in amounts of from about 0.01% to about 1%, and potassium in amounts of from about 0.01% to about 1%, and methods comprising administering such compositions to patients susceptible to or suffering from kidney disease for the purpose of preventing or treating kidney disease.

11 Claims, No Drawings

(56) References Cited

OTHER PUBLICATIONS

Terumo Press Release, Dec. 11, 1998.
Terumo Product Catalog, Jun. 2005.
Brown et al., 1991, "Beneficial Effects of Dietary Mineral Restriction in Dogs with Marked Reduction of Functional Renal Mass," J. Amer. Society of Nephrology 1:1169-1179.
Brown, 1998, "Management of Feline Chronic Renal Failure," Waltham Focus 8(3):27-31.
Jacob et al., 2002, "Clinical Evaluation of Dietary Modification for Treatment of Spontaneous Chronic Renal Failure in Dogs," J. Amer. Veterinary Medical Assoc. 220(8):1163-1170.
Lin, 1999, "Dog and Cat Chronic Renal Organ Failure Food Therapy," Chinese J. Veterinary Medicine (Series 25) 12:54.
Markwell, 1998, "Dietary Management of Renal Failure in the Dog and Cat," Waltham Focus 8(2):16-22.
Polzin et al., 2000, "Dietary Management of Feline Chronic Renal Failure: Where Are We Now? In What Direction Are We Headed?" J. Feline Medicine and Surgery 2:75-82.
Adams et al., 1994, Am. J. Vet. Res. 54:1653-1662.
Brown et al., "Effects of dietary polyunsaturated fatty acid supplementation in early renal insufficiently in dogs," J Lab Clin Med., Mar. 2000, 135(3):275.

* cited by examiner

METHODS AND COMPOSITIONS FOR THE PREVENTION AND TREATMENT OF KIDNEY DISEASE

CROSS-REFERENCE TO RELATED APPLICATIONS

This application claims priority to U.S. Provisional Application Ser. No. 60/695,152 filed Jun. 29, 2005, the disclosure of which is incorporated herein by reference.

BACKGROUND OF THE INVENTION

1. Field of the Invention

This invention relates generally to compositions and methods for combating kidney disease and particularly to the use of food compositions for preventing or treating kidney disease.

2. Description of the Prior Art

Chronic kidney disease currently affects as many as 20 million Americans. Unfortunately, the incidence and prevalence of the disease have doubled in the past few years. The increase is most likely attributable to improved treatments for hypertension, diabetes, and coronary disease. These improvements have increased the longevity for affected patients and, therefore, their likelihood of developing chronic kidney disease. Estimated medical and other economic costs of chronic kidney disease are expected to approach $28 billion annually within a few years.

The effect of dietary protein restriction on kidney disease is the subject of debate. Some studies suggest that dietary protein restriction slows the progression of kidney disease, particularly in patients with diabetes (Pedrini M T, Levey A S, Lau J, Chalmers T C, Wang P H. The effect of dietary protein restriction on the progression of diabetic and nondiabetic renal diseases: a meta-analysis. Ann Intern Med 1996; 124: 627-32). However, these studies were inconclusive by the use of ACE-inhibitor therapy on the rate of disease progression. One study attempted to determine a level of protein intake that might reduce the risk of kidney disease progression and also minimize the risk of malnutrition (Klahr S, Levey A S, Beck G J, Caggiula A W, Hunsicker L, Kusek J W, et al. The effects of dietary protein restriction and blood-pressure control on the progression of chronic renal disease. Modification of Diet in Renal Disease Study Group. N Engl J Med 1994; 330:877-84). The study evaluated three levels of dietary protein intake and found that a very-low-protein diet slightly decreased the rate of progression of proteinuria compared with diets with higher protein intake. The very-low-protein diet did not result in malnutrition but it also did not decrease the progression of kidney disease.

Further, diets that contain very low amounts of protein and other nutrients may be beneficial for preventing or treating kidney disease but can cause undesirable weight loss and muscle wasting. In contrast, diets that have higher amounts of protein and other nutrients are generally not useful for preventing or treating kidney disease. Similarly, there is no useful information on the combination of nutrients that can be used to prevent or treat kidney disease. There is, therefore, a need for food compositions having defined ranges of protein and other nutrients that are beneficial for preventing or treating kidney disease while avoiding the undesirable weight loss and muscle wasting.

SUMMARY OF THE INVENTION

It is, therefore, an object of the present invention to provide compositions and methods for preventing or treating kidney disease.

It is another object of the invention to provide articles of manufacture in the form of kits that contain combinations of compositions and devices useful for preventing or treating kidney disease.

It is a further object of the invention to provide a means for communicating information about or instructions for using a food composition comprising one or more food ingredients containing relatively low amounts of protein, sodium, and potassium for preventing or treating kidney disease.

These and other objects are achieved using novel compositions and methods for preventing or treating kidney disease. The compositions comprise one or more food ingredients containing relatively low amounts of protein, sodium, and potassium, typically protein in amounts of from about 5% to about 40%, sodium in amounts of from about 0.01% to about 1%, and potassium in amounts of from about 0.01% to about 1%. The methods comprise administering such compositions to patients susceptible to or suffering from kidney disease. Kits comprising a food composition in combination with renal drugs, renal diagnostic devices, and means for communicating information about and instructions for using the invention are also provided.

Other and further objects, features, and advantages of the present invention will be readily apparent to those skilled in the art.

DETAILED DESCRIPTION OF THE INVENTION

Definitions

The term "patient" means a human or other animal susceptible to or suffering from kidney disease, including avian, bovine, canine, equine, feline, hircine, murine, ovine, and porcine animals. Preferably, the patient is a canine or feline.

The term "relatively low amounts" means amounts of protein, sodium, and potassium that prevent or treat kidney disease but not amounts that are so low that they cause undesirable weight loss and muscle wasting.

The term "extremely low amounts" means amounts of protein, sodium, potassium that may prevent or treat kidney disease but amounts that are so low that they cause undesirable weight loss and muscle wasting.

The term "renal drug" means any compound, composition, or drug useful for preventing or treating kidney disease.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The term "in conjunction" means that one or more of the compositions and compounds (e.g., renal drugs or composition components) of the present invention are administered to a patient (1) together in a food composition or (2) separately at the same or different frequency using the same or different administration routes at about the same time or periodically. "Periodically" means that the compositions, food compositions, and compounds are administered on a dosage schedule acceptable for a specific composition, food composition, and compound and that the food compositions are administered or fed to a patient routinely as appropriate for the particular patient. "About the same time" generally means that the compositions, composition components, renal drugs, and food compositions are administered at the same time or within about 72 hours of each other. In conjunction specifically includes administration schemes wherein renal drugs are administered for a prescribed period and the compositions are administered indefinitely.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a method" or "a food composition" includes a plurality of such methods or compositions. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compounds, processes, techniques, procedures, technology, articles, and other compositions and methods disclosed therein that might be used with the present invention. However, nothing herein is to be construed as an admission that the invention is not entitled to antedate such disclosure by virtue of prior invention.

The Invention

In one aspect, the present invention provides a food composition for preventing or treating kidney disease. The food composition comprises one or more food ingredients containing relatively low amounts of protein, sodium, and potassium. The invention is based upon the novel discovery that kidney function can be altered by administering the composition to a patient and that altering kidney function with the composition can prevent or treat kidney disease. The composition contains a novel combination of ingredients in specific amounts that have been found to be useful to prevent and/or treat kidney disease.

In one embodiment, the food composition comprises one or more food ingredients containing protein in amounts of from about 5% to about 40%, sodium in amounts of from about 0.01% to about 1%, and potassium in amounts of from about 0.01% to about 1%. In another embodiment, the food composition comprises one or more food ingredients containing protein in amounts of from about 8% to about 25%, sodium in amounts of from about 0.05% to about 0.6%, and potassium in amounts of from about 0.05% to about 0.6%. in a further embodiment, the food composition comprises one or more food ingredients containing protein in amounts of from about 10% to about 16%, sodium in amounts of from about 0.1% to about 0.5%, and potassium in amounts of from about 0.1% to about 0.5%.

All percentages expressed herein are on a weight by dry matter basis unless specifically stated otherwise. In a further, embodiment, the food composition comprises one or more food ingredients containing protein in amounts of from about 5% to about 30%, sodium in amounts of from about 0.01% to about 2%, potassium in amounts of from about 0.01% to about 2%, and phosphorous in amounts of from about 0.2% to about 1%.

The food ingredients useful in the present invention include any food ingredient suitable for consumption by a patient. Typical food ingredients include but are not limited to fats, carbohydrates, proteins, fibers, and nutrients such as vitamins, minerals, and trace elements. Skilled artisans can select the amount and type of food ingredients for a typical food based upon the dietary requirements of the patient, e.g., the patient's species, age, size, weight, health, and function.

The food composition can comprise 100% of any particular food ingredient or can comprise a mixture of food ingredients in various proportions. in preferred embodiments, the food composition comprises a combination of food ingredients in amounts of from about 5% to about 40% protein, from about 0.01% to about 1% sodium, from about 0.01% to about 1% potassium, from about 0% to about 50% fat, from about 0% to about 75% carbohydrate, from about 0% to about 40% dietary fiber, and from about 0% to about 15% of one or more nutrients.

The fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

The protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like. Meat by-products include lungs, kidneys, brain, livers, stomachs, and intestines. The protein food ingredient may also be free amino acids and/or peptides. Preferably, the protein food ingredient comprises meat, a meat by-product, dairy products, or eggs.

The fiber food ingredient is obtained from a variety of sources such as vegetable fiber sources, e.g., cellulose, beet pulp, peanut hulls, and soy fiber.

The nutrients are obtained from a variety of sources known to skilled artisans, e.g., vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

The food compositions may contain additions ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of patient; the patient's age, body weight, general health, sex, and diet; the patient's consumption rate; the type of kidney disease being treated; and the like. Therefore, the component and ingredient amounts may vary widely and may deviate from the preferred proportions described herein.

The food compositions may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, e.g., direct steam injection or using a vessel fitted with a heat exchanger. Following the addition of the last ingredient, the mixture is heated to a temperature of from about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

The food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into dry food pieces.

The food compositions can be in any form useful for feeding the composition to a patient, e.g., kibbles, treats, and toys for animal food. Kibbles are generally formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavors, fats, oils, powders, and the like. Kibble also can be made from the dough using a baking process, rather than extrusion, wherein the dough is placed into a mold before dry-heat processing. Treats include compositions that are given to an animal to entice the animal to eat during a non-meal time, e.g., dog bones or biscuits for canines. Treats may be nutritional wherein the composition comprises one or more nutrients or and may have a food-like composition. Non-nutritional treats encompass any other treats that are non-toxic. The composition or components are coated onto the treat, incorporated into the treat, or both. Treats of the present invention can be prepared by an extrusion or baking process similar to those used for dry food. Other processes also may be used to either coat the composition on the exterior of existing treat forms or inject the composition into an existing treat form. Toys include chewable toys such as artificial bones and food compositions shaped to resemble natural foods that are appealing to the animal. The food composition of the present invention can comprise the toy or can form a coating on the surface of the toy or on the surface of a component of the toy. The composition can be incorporated partially or fully throughout the toy or both. In one embodiment, the composition is orally accessible by the intended user. There are a wide range of suitable toys known to skilled artisans, e.g., as shown in U.S. Pat. Nos. 5,339,771 and 5,419,283. The present invention encompasses partially consumable toys, e.g., toys comprising plastic components, and fully consumable toys, e.g., various artificial bones and similar foods. Further, the invention encompasses toys for both human and non-human use, particularly toys for companion, farm, and zoo animal use, and more particularly for feline and canine use.

In another aspect, the present invention provides the food compositions of the present invention further comprising one or more renal drugs. Renal drugs useful in the invention are any renal drugs known to skilled artisans to be useful for combating kidney disease. Preferred drugs include lysosome-activating compounds such as those described in U.S. Pat. No. 6,589,748, triterpene saponins such as those described in U.S. Pat. No. 6,784,159, activin inhibitors such as those described in U.S. Pat. No. 6,599,876 and US Patent Application Number (USPAN) 20020028762, integrin receptor inhibitors and TGF inhibitors such as those described in U.S. Pat. No. 6,492,325, TGF activation inhibitors such as those described in U. S. Pat. No. 6,458,767, and insulin-like growth factor (IGF) as described in U.S. Pat. No. 5,723,441. Most preferred drugs include Converting Enzyme (ACE) inhibitors, androgens, erythropoiten, and calcitriol. Angiotensin and endothelin are potent systemic vasoconstrictors with specific intrarenal effects that contribute to progressive renal injury. A variety of renal drugs are used to mitigate the effect of these vasoconstrictors. Angiotensin converting enzyme inhibitors (enalapril—Enacard and Vasotec and benazepril—Lotensin) have been associated with a reduction in the severity of proteinuria and slowing of progression of renal failure. The ACE inhibitor enalapril (Enacard, Vasotec) limits glomerular and systemic hypertension, proteinuria, and glomerular and tubulointerstitial lesions. Angiotensin blockers and endothelin inhibitors have beneficial effects in renal disease. Vasopeptide inhibitors are agents that inhibit both ACE and neutral endopeptidase, an enzyme involved in the breakdown of natriuretic peptides, adrenomedullin, and bradykinin. These renal drugs decrease angiotenin II production and increase accumulation of vasodilators. Renal patients with systemic hypertension respond to calcium channel blockers such as amlodipine (Norvasc). Uremic gastritis (esophagitis, gastritis, gastric ulceration and hemorrhage) is treated with H2 receptor antagonists (cimetidine—Tagamet, famotidine—Pepcid), proton pump blockers (omeprazole—Prilosec), cytoprotective agents (misoprostol—Cytotec), and antiemetic drugs that effect the emetic center (chlorpromazine—Thorazine, perchlorperazine—Compazine, metoclopramide—Reglan). Androgens or anabolic steroids (Stanozol, Winstrol—V) are used in the treatment of anemia associated with chronic renal failure. Hormone replacement therapy using recombinant human (or other species) erythropoiten (Epoetin alpha, Epogen, Procrit) is the treatment of choice for severe anemia associated with renal failure. Phosphate binders (aluminum hydroxide—Amphojel, aluminum carbonate—Basaljel) are used to control hyperphosphatemia and secondary renal hyperparathyroidism. Calcitriol (1, 25-dihydroxycholecalciferol) (Rocaltrol) and vitamin D analogues cause a calcium-independent suppression of parathyroid hormone (PTH). Administration of phosphate binders, calcitriol and related compounds has been advocated in chronic renal failure to prevent multi-system toxicity caused by PTH. Potassium depletion and hypokalemia are common in cats with chronic renal failure. Oral supplementation of potassium in the form of potassium gluconate (Tumil K, RenaKare, Kolyum) or citrate is recommended. Holistic renal drugs and compositions are also included in the present invention. Preferred holistic renal drugs include cranberry extract and mannose. Cranberry extract is purported to reduce the prevalence of urinary tract infection which is a common risk factor for long-term decline of renal function. Renal drugs include typical small molecule pharmaceuticals, small proteins, macromolecular proteins and molecules, and antibodies and further include vaccines designed to prevent renal disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The renal drugs are administered to the patient using any method appropriate for the renal drug and in amounts known to skilled artisans to be sufficient to treat or prevent renal disease.

In a further aspect, the present invention provides a method for preventing or treating kidney disease. The method comprises feeding a patient a food composition comprising one or more food ingredients containing relatively low amounts of protein, sodium, and potassium. The method further comprises feeding a patient a food composition comprising one or more food ingredients containing relatively low amounts of protein, sodium, and potassium in conjunction with a kidney disease preventing or treating amount of a renal drug.

In another aspect, the present invention provides a method for preventing or treating kidney disease. The method comprises feeding a patient a food composition comprising one or more food ingredients containing relatively low amounts of protein. This aspect of the invention is based upon the novel discovery that food compositions containing protein is certain amounts can prevent or treat kidney disease while not causing the undesirable weight loss and muscle wasting characteristic of previously known food compositions having very low amounts of protein. In various embodiments, the food composition useful in the method comprises one or more food ingredients containing protein in amounts of from about 5% to about 40%, preferably from about 8% to about 25%, most preferably from about 10% to about 16%. The invention also provides a food composition for preventing or treating kidney disease comprising one or more food ingredients containing relatively low amounts of protein, preferably in amounts of from about 5% to about 40%, more preferably from about 8% to about 25%, most preferably from about 10% to about 16%. In a further, embodiment, the method comprises feeding a patient a food composition comprising one or more food ingredients containing protein in amounts of from about 5% to about 30%, sodium in amounts of from about 0.01% to about 2%, potassium in amounts of from about 0.01% to about 2%, and phosphorous in amounts of from about 0.2% to about 1%.

In another aspect, the present invention provides a method for manufacturing a food composition suitable for preventing or treating renal disease. The method comprises admixing a food composition containing extremely low amounts of one or more of protein, sodium, and potassium and one or more supplements containing sufficient protein, sodium, or potassium to produce a food composition containing relatively low amounts of protein, sodium, and potassium when the supplement(s) are admixed with the food composition containing extremely low amounts of one or more of protein, sodium, and potassium. In one embodiment, the food composition comprises one or more food ingredients containing protein in amounts of from about 5% to about 40%, sodium in amounts of from about 0.01% to about 1%, and potassium in amounts of from about 0.01% to about 1%.

In a further aspect, the present invention provides a kit comprising in separate containers in a single package a food composition containing extremely low amounts of one or more of protein, sodium, and potassium and one or more supplements containing sufficient protein, sodium, or potassium to produce a food composition containing relatively low amounts of protein, sodium, and potassium when the supplement(s) are admixed with the food composition containing extremely low amounts of one or more of protein, sodium, and potassium. The supplements can be food compositions containing protein, sodium, and\or potassium or can be compounds or other compositions suitable for consumption by a patient. Foods, minerals, and trace elements known to contain enriched amounts of protein, sodium, and potassium are particularly useful. Supplements useful for other diseases such as arthritis and supplements useful for cleaning teeth and ensuring fresh breath can be included, e.g., EPA, glucosamine, chondroitin sulfate, and SAMe. In other embodiments, the kit further comprises in separate containers in a single package or in separate containers in a virtual package, as appropriate for the kit component, at least one of (1) a renal drug, (2) a renal diagnostic device, (3) a means for communicating information about or instructions for admixing a food composition containing extremely low amounts of one or more of protein, sodium, and potassium and one or more supplements containing sufficient protein, sodium, or potassium to produce a food composition containing relatively low amounts of protein, sodium, and potassium when the supplement(s) are admixed with the food composition containing extremely low amounts of one or more of protein, sodium, and potassium, (4) a means for communicating information about or instructions for using a food composition comprising one or more food ingredients containing relatively low amounts of protein, sodium, and potassium for preventing or treating kidney disease, (5) a means for communicating information about or instructions for administering in conjunction a food composition comprising one or more food ingredients containing relatively low amounts of protein, sodium, and potassium and a renal drug for preventing or treating kidney disease, and (6) a means for communicating information about or instructions for administering in conjunction a food composition comprising one or more food ingredients containing relatively low amounts of protein, sodium, and potassium and using renal diagnostic devices for determining kidney function and evaluating the presence and severity of renal insufficiency or dysfunction. The kit components are typically in a separate package, in or on the package with one of the other kit components, or in a virtual package, as appropriate for the type of kit component. When the kit comprises a virtual package, the kit is limited to the instructions in a virtual environment in combination with one or more of the other physical kit components.

In an additional aspect, the present invention provides a kit comprising in separate containers in a single package or in separate containers in a virtual package, as appropriate, a food composition comprising one or more food ingredients containing relatively low amounts of protein, sodium, and potassium and at least one of (1) a renal drug, (2) a renal diagnostic device, (3) a means for communicating information about or instructions for admixing a food composition containing extremely low amounts of one or more of protein, sodium, and potassium and one or more supplements containing sufficient protein, sodium, or potassium to produce a food composition containing relatively low amounts of protein, sodium, and potassium when the supplement(s) are admixed with the food composition containing extremely low amounts of one or more of protein, sodium, and potassium, (4) a means for communicating information about or instructions for using a food composition comprising one or more food ingredients containing relatively low amounts of protein, sodium, and potassium for preventing or treating kidney disease, (5) a means for communicating information about or instructions for administering in conjunction a food composition comprising one or more food ingredients containing relatively low amounts of protein, sodium, and potassium and a renal drug for preventing or treating kidney disease, and (6) a means for communicating information about or instructions for administering in conjunction a food composition comprising one or more food ingredients containing relatively low amounts of protein, sodium, and potassium and using renal diagnostic devices for determining kidney function and evaluating the presence and severity of renal insufficiency or dysfunction. The kit components are typically in a separate package, in or on the package with one of the other kit components, or in a virtual package, as appropriate for the type of kit component. When the kit comprises a virtual package, the kit is limited to the instructions in a virtual environment in combination with one or more of the other physical kit components.

The food composition in a kit comprises one or more food ingredients containing relatively low amounts of protein, sodium, and potassium.

In some embodiments, the kits contain one or more renal diagnostic devices for determining kidney function and evaluating the presence and severity of renal insufficiency or dysfunction in a patient. The renal diagnostic devices are typically in a separate package but may be in the package with one of the other kit components. The renal diagnostic devices useful in the present invention include any device suitable for determining kidney function and evaluating the presence and severity of renal insufficiency or dysfunction in an animal. Preferred diagnostic methods include serum urea nitrogen (SUN), creatinine levels, urine specific gravity, and DNA damage, including urine assays for albumin such as those described in U.S. Pat. Nos. 6,589,748, 6,447,989 and USPAN 20050026225 and comet trail assays. Diagnostic methods are based upon known techniques including (1) blood markers such as elevated blood urea nitrogen concentration, elevated serum creatinine concentration, hyperphosphatemia, hyperkalemia or hypokalemia, metabolic acidosis and hypoalbuminemia, (2) urine markers such as impaired urine concentrating ability, proteinuria, cylinduria, renal hematuria, inappropriate urine pH, inappropriate urine glucose concentration, and cystinuria, (3) physical, imaging, and diagnostic markers such as size, shape, location, and density, (4) single nucleotide polymorphisms (SNPs) such as those disclosed in WO 2004113570 A2, (5) genetic profiles that are indicative of renal insufficiency or dysfunction, (6) proteomic profiles that are indicative of renal insufficiency or dysfunction, and (7) metabolic profiles that are indicative of renal insufficiency or dysfunction. These diagnostic methods and devices (e.g., test strips, ELISA assays, comet assays,) based upon such methods are commonly available to skilled artisans such as scientists and health care professionals and many are available to consumers, e.g., the Heska Corporation's (Fort Collins Colo.) E.R.D.-HealthScreen Urine Tests that detects small amounts of albumin in the urine ("microalbuminuria").

The kits provide a food composition comprising one or more food ingredients containing protein in amounts of from about 5% to about 40%, sodium in amounts of from about 0.01% to about 1%, and potassium in amounts of from about 0.01% to about 1%.

In another aspect, the present invention provides a means for communicating information about or instructions for (1) using a food composition containing relatively low amounts of protein, sodium, and potassium for preventing or treating kidney disease, (2) administering in conjunction a food composition comprising one or more food ingredients containing relatively low amounts of protein, sodium, and potassium and a renal drug for preventing or treating kidney disease, (3) admixing and administering a food composition containing extremely low amounts of one or more of protein, sodium, and potassium and one or more supplements containing sufficient protein, sodium, or potassium to produce a food composition containing relatively low amounts of protein, sodium, and potassium when the supplement(s) are admixed with the food composition containing extremely low amounts of one or more of protein, sodium, and potassium, (4) using a kit of the present invention for preventing or treating renal disease, and (5) administering in conjunction a food composition comprising one or more food ingredients containing relatively low amounts of protein, sodium, and potassium and using renal diagnostic devices for determining kidney function and evaluating the presence and severity of renal insufficiency or dysfunction. The communicating means comprises a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for manufacturing and/or administering the food compositions of the invention and renal drugs, (2) information for using the renal diagnostic devices, (3) details about the side effects, if any, caused by using the present invention in combination with other drugs, and (4) contact information for patients to use if they have a question about the invention and its use. Useful instructions include dosages, administration amounts and frequency, and administration routes. The communication means is useful for instructing a patient on the benefits of using the present invention and communicating the approved methods for administering the invention to a patient.

The compositions, methods, and kits are useful for decreasing the morbidity and mortality for patients susceptible to or suffering from kidney disease.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

Canine Study

Study Design: This study utilized 10 healthy geriatric beagle dogs (10 years old or over) per group (40 dogs total).

The dogs were determined to be healthy by physical exam and blood chemistry screen. Dogs with confirmed renal failure, cancer, arthritis, hypothyroidism or other diseases were excluded. The dogs were cared for in accordance with Institutional Animal Care and Use Committee protocols. The study design utilized a 30 day pre-feeding period followed by a 6 month test feeding period for a total of 7 months.

During the 30 day pre-feeding period, all dogs were fed a control formula food. During the last week of the pre-feeding period, blood and urine samples were taken from each animal. Dual-energy x-ray absorptiometry (DXA) scans pressure map analysis were also performed. The dogs were then blocked by age, gender and body fat percentage and assigned to 4 different treatment groups. Each group of dogs was randomly assigned to receive either the new Geriatric food or one of three competitor products.

During the 7 month test period, blood samples were drawn at 1 month, 3 months and 6 months for analysis of biomarkers. Dogs were scanned by DXA at 3 months and 6 months to document changes in body composition and bone density. To assess changes in kidney health, urine microalbuminuria tests were performed at 3 months and 6 months. Throughout the duration of the study, body weights were recorded weekly and food intake recorded daily. Additionally, dogs were offered enrichment toys, received routine grooming and had daily opportunities for socialization with other dogs and people. Blood samples were also collected to determine proteomic/genomic marker differences over time.

Removal Criteria: If dogs were diagnosed with renal disease, cancer, hypothyroidism, Cushings or other disease, they were removed from the study and received treatment appropriate for their disease condition. In addition, dogs that refused to eat at least 25% of their assigned food for more than 4 days or had weight loss that exceeds 2.0%/weekly, they were removed from the study. Other health issues or conditions that arose during the study, such as diarrhea, were monitored and treated as needed while attempting to maintain the dogs on the assigned treatment foods. If the necessary treatment involved switching dogs to another food for more than 4 days, the dog was removed from the study.

Data was taken according to the Study Schedule shown below. The foods used in the study are shown in Table 1. The data were collected using the Analytical Methods shown herein. The study was conducted using the Feeding and/or Treatment Administration regime shown below.

| Study Schedule | | | |
|---|---|---|---|
| Study Day | Procedure | Measurement | Sample |
| Pre-Feeding Period | | | |
| Days 0-30 | All dogs receive Control Food | Food Intake daily Body Weight - weekly | |
| Day 30 | Block by age, gender, body fat & assign to groups & foods | | 10 ml blood - Biomarkers & chemistry Screen 5 ml Urine-microalbuminuria & specific gravity |
| Test Feeding Period | | | |
| Days 31-210 | Each group of dogs receive assigned food | Food intake - daily Body weight - weekly | 10 ml blood - Biomarkers and chemistry screen (day 61, 121, 211) 5 ml Urine-microalbuminuria and specific gravity (day 61, 121, 211) |

TABLE 1

Analyzed Nutrient Profiles of the Four Foods Utilized in the Study

| Nutrients, 100% Dry Matter Basis | Food 61522 | Food 62292 | Food 62794 | Food 62814 |
|---|---|---|---|---|
| Crude Protein, % | 20.10 | 27.65 | 27.76 | 29.39 |
| Fat, % | 16.45 | 13.52 | 11.08 | 13.59 |
| Ca, % | 0.71 | 0.79 | 1.28 | 1.35 |
| P, % | 0.61 | 0.68 | 0.93 | 1.14 |
| EPA, % | 0.32 | 0.10 | <0.01 | 0.10 |
| Total n-3 fatty acids, % | 1.30 | 0.48 | 0.13 | 0.41 |
| Total n-6 fatty acids, % | 3.96 | 3.10 | 1.79 | 2.66 |
| Taurine, ppm | 1400 | 1090 | <100 | 1600 |
| Carnitine, ppm | 314 | 55 | 19 | 84 |
| Methionine, % | 1.00 | 0.49 | 0.51 | 0.66 |
| Cystine, % | 0.25 | 0.43 | 0.47 | 0.34 |
| Manganese, ppm | 87 | 77 | 71 | 69 |
| Vitamin E, IU/kg | 1492 | 594 | 894 | 421 |
| Vitamin C, ppm | 127 | 288 | 86 | 21 |

Analytical Methods

Urine Samples Microabluminuria were performed on all urine samples collected during the study.

Blood Samples Blood samples collected on days 0, 30 and 90 were analyzed for arthritic markers, antioxidant status markers, fatty acids, amino acids and chemistry screen to ensure the health of all animals on the study.

| Feeding and/or Treatment Administration Food 61526 | | | |
|---|---|---|---|
| Weight (lbs) | kcal/Day | Dry Food Amount per Day (cups) | Dry Food Amount per Day (cups) |
| 0.5 | 37 | 1/8 | 1/8-1/8 |
| 1 | 62 | 1/8 | 1/8-1/4 |
| 1.5 | 84 | 1/4 | 1/4-1/4 |
| 2 | 104 | 1/3 | 1/4-1/3 |
| 2.5 | 123 | 1/3 | 1/3-3/8 |
| 3 | 141 | 3/8 | 1/3-1/2 |
| 4 | 175 | 1/2 | 3/8-5/8 |
| 5 | 207 | 5/8 | 1/2-2/3 |
| 6 | 237 | 2/3 | 5/8-3/4 |
| 7 | 266 | 3/4 | 5/8-7/8 |
| 8 | 294 | 7/8 | 2/3-1 |
| 9 | 322 | 7/8 | 3/4-1 |
| 10 | 348 | 1 | 7/8-1 1/8 |
| 15 | 472 | 1 1/3 | 1 1/8-1 1/2 |
| 20 | 585 | 1 2/3 | 1 3/8-1 7/8 |
| 25 | 692 | 2 | 1 5/8-2 1/4 |
| 30 | 794 | 2 1/4 | 1 7/8-2 5/8 |
| 40 | 985 | 2 3/4 | 2 1/3-3 1/4 |
| 50 | 1164 | 3 1/4 | 2 3/4-3 7/8 |

-continued

Feeding and/or Treatment Administration Food 61526

| 60 | 1335 | 3¾ | 3⅛-4⅜ |
| 70 | 1498 | 4¼ | 3½-4⅞ |
| 80 | 1656 | 4⅔ | 3⅞-5⅜ |
| 90 | 1809 | 5⅛ | 4⅓-5⅞ |
| 100 | 1958 | 5½ | 4⅝-6⅜ |

Food 62794

| Weight, lbs | Weight, kg | Minimum food, g | Mid point food, g | Maximum, food, g |
| --- | --- | --- | --- | --- |
| 3-12 | 1.4-5.5 | 53 | 93 | 133 |
| 13-20 | 5.9-9.1 | 133 | 160 | 186 |
| 21-35 | 9.5-15.9 | 186 | 226 | 265 |
| 36-50 | 16.4-22.7 | 265 | 305 | 345 |
| 51-75 | 23.2-34.1 | 345 | 398 | 451 |
| 76-100 | 34.5-45.5 | 451 | 504 | 557 |
| Over 100 | 45.5+ | | | |

Based on standard 8 oz cup (351 kcal/cup, 1510 kcal/lb, 3.3 kcal/gram, 106 gram/cup)

Amounts are recommended for an average adult dog with normal activity. Food intake requirements vary depending on age, activity, and environment, and should be adjusted accordingly.

Food 62814

| Weight, lbs | Weight, kg | Minimum, Grams/day |
| --- | --- | --- |
| 3 | 1.4 | 25 |
| 10 | 4.5 | 80 |
| 20 | 9.1 | 115 |
| 30 | 13.6 | 150 |
| 40 | 18.2 | 185 |
| 50 | 22.7 | 215 |

These guideline amounts are a starting point and your dog may need more food depending upon age, activity and temperament. To reach an optimal body condition, you may need to adjust food intake. Feed this formula to dogs up to 100 lbs, who are 7 years and older.

Food 62292

| Weight, lbs | Weight, kg | Indoor | Activity (1 hr) | Activity (2 hr) |
| --- | --- | --- | --- | --- |
| 26.4 | 12 | 165 | 185 | 205 |
| 30.8 | 14 | 185 | 205 | 230 |
| 35.2 | 16 | 200 | 230 | 255 |
| 39.6 | 18 | 220 | 250 | 275 |
| 44.0 | 20 | 240 | 270 | 300 |
| 48.4 | 22 | 255 | 285 | 320 |
| 52.8 | 24 | 270 | 305 | 340 |
| 55.0 | 25 | 280 | 315 | 350 |

Optimal feeding amounts may vary with age, temperament and environment.

Example 2

Feline Study

Study Design: This study utilized 10 healthy geriatric cats (12 years old or over) per group (40 cats total). The cats were determined to be healthy by physical exam and blood chemistry screen. Cats with confirmed renal failure, cancer, arthritis, hyperthyroidism or other diseases were excluded. The cats were located in the Hill's Pet Nutrition Center (Topeka, Kans.) and were cared for in accordance with Institutional Animal Care and Use Committee protocols. The study design utilized a 30 day pre-feeding period followed by a 6 month test feeding period for a total test period of 7 months.

During the 30 day pre-feeding period, all cats were fed the control formula food (Science Diet Senior without the antioxidant package). During the last week of the pre-feeding period, blood samples taken and DXA scans were performed. The cats were then blocked by age, gender and body fat percentage and assigned to 3 different groups. Each group of cats was randomly assigned to receive either the new geriatric food or one of three competitor products. All foods were formulated to meet or exceed AAFCO nutrient recommendations.

During the 7 month test period, blood samples were taken at 1 month, 3 months and 6 months for analysis of biomarkers. Cats were scanned by DXA at 3 months and 6 months to document changes in body composition and bone density. To assess changes in kidney health, urine microalbuminuria tests were performed at 1 month, 3 months and 6 months. Throughout the duration of the study, body weight was recorded weekly and food intake recorded daily. Additionally, cats were offered enrichment toys, received routine grooming and had daily opportunities for socialization with other cats and people.

Removal Criteria: If at any point in the study, cats were diagnosed with renal disease, cancer, hyperthyroidism, or other disease, they were removed from the study and received treatment appropriate for their disease condition. In addition, cats that refuse to eat at least 25% of their assigned food for more than 4 days or had weight loss that exceeds 2.0%/week, were removed from the study. Other health issues or conditions that arose during the study, such as diarrhea, were monitored and treated as needed while attempting to maintain the cats on the assigned treatment foods. If the necessary treatment involved switching cats to another food for more than 4 days, the cat was removed from the study.

Data was taken according to the Study Schedule shown below. The foods used in the study are shown in Table 2. The data were collected using the Analytical Methods shown herein. The study was conducted using the Feeding and/or Treatment Administration regime shown below.

The results of the study were analyzed to determine the affects of various foods, food components, and nutrients on the kidney and their usefulness for the prevention and/or treatment of kidney disease. The results show that relatively low levels of protein, sodium, and potassium are beneficial for preventing and/or treating kidney disease.

Study Schedule

| Study Day | Procedure | Measurement | Sample |
| --- | --- | --- | --- |
| Pre-Feeding Period | | | |
| Days 0-30 | All cats receive Control Food | Food Intake daily Body weight-weekly | |
| Day 30 | Block by age, gender, body fat & assign to groups & foods | | 10 ml blood - Biomarkers & chemistry Screen 5 ml Urine-microalbuminuria & specific gravity |

-continued

| Study Schedule | | | |
|---|---|---|---|
| Study Day | Procedure | Measurement | Sample |
| Test Feeding Period | | | |
| Days 31-210 | Each group of dogs receive assigned food | Food intake - daily Body weight - weekly | 10 ml blood - Biomarkers and chemistry screen (day 61, 121, 211) 5 ml Urine-micro-albuminuria and specific gravity (day 61, 121, 211) |

TABLE 2

Analyzed Nutrient Profiles of the Four Foods Utilized in the Study

| Key Nutrients, 100% Dry Matter Basis | Food 61526 | Food 62264 | Food 62695 | Food 62779 |
|---|---|---|---|---|
| Crude Protein, % | 35.73 | 34.85 | 30.52 | 40.45 |
| Fat, % | 22.47 | 15.39 | 23.63 | 15.69 |
| Ca, % | 0.94 | 1.22 | 0.80 | 1.38 |
| P, % | 0.77 | 1.05 | 0.72 | 1.30 |
| DHA, % | 0.23 | 0.08 | 0.11 | 0.07 |
| EPA, % | 0.32 | 0.07 | 0.13 | 0.07 |
| Total n-3 fatty acids, % | 1.14 | 0.28 | 0.74 | 0.32 |
| Total n-6 fatty acids, % | 5.09 | 2.87 | 5.02 | 2.13 |
| Taurine, ppm | 2100 | 1800 | 1600 | 2100 |
| Carnitine, ppm | 367 | 28 | 90 | 28 |
| Methionine, % | 1.32 | 1.05 | 0.72 | 0.77 |
| Cystine, % | 0.47 | 0.38 | 0.51 | 0.53 |
| Manganese, ppm | 104 | 63 | 70 | 73 |
| Vitamin E, IU/kg | 1292 | 390 | 608 | 964 |
| Vitamin C, ppm | 141 | 12 | 511 | 110 |

Analytical Methods

Urine Samples Microablumeria were performed on all urine samples collected during the study.

Blood Samples Blood samples collected on days 30, 59 and 120 and 210 were analyzed for arthritic markers, antioxidant status markers, fatty acids, amino acids and chemistry screen to ensure the health of all animals on the study.

| Feeding and/or Treatment Administration Food 61526 | | | |
|---|---|---|---|
| Weight (lbs) | kcal/Day | Dry Food Amount per Day (cups) | Dry Food Amount per Day (cups) |
| 0.5 | 28 | 1/8 | 1/8-1/8 |
| 1 | 46 | 1/8 | 1/8-1/8 |
| 1.5 | 63 | 1/8 | 1/8-1/8 |
| 2 | 78 | 1/4 | 1/8-1/4 |
| 2.5 | 92 | 1/4 | 1/4-1/4 |
| 3 | 106 | 1/4 | 1/4-1/3 |
| 4 | 131 | 1/3 | 1/4-3/8 |
| 5 | 155 | 3/8 | 1/3-1/2 |
| 6 | 178 | 1/2 | 3/8-1/2 |
| 7 | 200 | 1/2 | 3/8-5/8 |
| 8 | 221 | 1/2 | 1/2-5/8 |
| 9 | 241 | 5/8 | 1/2-2/3 |
| 10 | 261 | 2/3 | 1/2-3/4 |
| 15 | 354 | 7/8 | 3/4-1 |

| Food 62779 | | | | |
|---|---|---|---|---|
| Weight, lbs | Weight, kg | Minimum food, g | Mid point food, g | Maximum, food, g |
| 5-9 | 2-4 | 35 | 44 | 53 |
| 10-14 | 4-6 | 71 | 89 | 106 |

It is important that you feed Purina ONE to your adult cat "free choice" throughout the day, rather than as just a single feeding only at mealtime. Food intake required to maintain ideal body condition will vary, depending on age, activity, and environment. Watch your cat's weight and adjust food amounts accordingly. If you have a kitten, pregnant or nursing cat you should continue feeding ONE Growth and Development formula for kittens.

| Food 62264 | | | | |
|---|---|---|---|---|
| Weight, lbs | Weight, kg | Minimum food, g | Mid point food, g | Maximum, food, g |
| 4 | 2 | 25 | 30 | 35 |
| 8 | 4 | 50 | 60 | 70 |
| 12 | 6 | 75 | 88 | 100 |
| 16 | 8 | 95 | 115 | 135 |
| 22 | 10 | 120 | 145 | 170 |

The chart lists the approximate amount of food your cat will need daily to maintain a healthy body weight (Portions are based on the use of a standard 8 ounce measuring cup). Your cat may eat more or less depending on age, temperament and activity. Adjust to maintain ideal body weight.

| Food 62695 | | | | |
|---|---|---|---|---|
| Weight, lbs | Weight, kg | Lean | Ideal | Overweight |
| 4-7 | 2-3 | 51 | 51 | 41 |
| 7-11 | 3-5 | 82 | 68 | 51 |
| 11-15 | 5-7 | 102 | 89 | 82 |
| 15-22 | 7-10 | 136 | 115 | 102 |

Standard 8 oz measuring cup = 102 grams. Optimal feeding amounts may vary according to your cat's temperament, activity level, and environment.

Calculations and Statistics

Data from both Examples were analyzed using General Linear Models procedure of SAS to determine treatment means. The experimental unit was dog or cat and day 0 was used as a covariate. The geriatric food was then compared to the three other foods. Differences were considered significant when $P<0.05$ and trends were determined when $P<0.10$.

Results

The results of the two studies were analyzed to determine the affects of various foods, food components, and nutrients on the kidney and their usefulness for the prevention and/or treatment of kidney disease. The results show that food compositions containing relatively low levels of protein, sodium, and potassium are beneficial for preventing and/or treating kidney disease.

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. An animal food composition comprising (i) animal protein in amounts of about 5% to about 40%, (ii) sodium in amounts of about 0.01% to about 1%, potassium in amounts of about 0.01% to about 1%, (iii) phosphorous in an amount at least 0.6%, (iv) eicosapentaenoic acid (EPA) in an amount at least 0.32%, (v) taurine in an amount of at least 1400 parts per million (ppm), and (vi) one or more ingredients selected from the group consisting of carnitine, methionine and cystine, each by weight on a dry matter basis, wherein the animal food composition is fed to a canine or feline.

2. The composition of claim 1 containing protein in amounts of from about 8% to about 25%, sodium in amounts of from about 0.05% to about 0.6%, potassium in amounts of from about 0.05% to about 0.6%, and taurine in amounts of about 1400 to about 2100 parts per million (ppm), each by weight on a dry matter basis.

3. The composition of claim 1 containing protein in amounts of from about 10% to about 20%, sodium in amounts of from about 0.1% to about 0.5%, potassium in amounts of from about 0.1% to about 0.5%, and taurine in amounts of about 1400 to about 2100 parts per million (ppm), each by weight on a dry matter basis.

4. The composition of claim 1 further comprising one or more renal drugs.

5. The composition of claim 4 wherein the renal drug is selected from the group consisting of Converting Enzyme (ACE) inhibitors, androgens, erythropoiten, angiotensin, endothelin, angiotensin converting enzyme inhibitors, calcium channel blockers, H2 receptor antagonists, proton pump blockers, and calcitriol.

6. A kit comprising in separate containers in a single package a food composition and one or more supplements, wherein when the food and the supplement are combined into a composition, the composition comprises (i) animal protein in amounts of about 5% to about 40%, (ii) sodium in amounts of about 0.01% to about 1%, (iii) potassium in amounts of about 0.01% to about 1%, (iv) phosphorous in an amount at least 0.6%, (v) eicosapentaenoic acid (EPA) in an amount at least 0.32%, (vi) taurine in an amounts of at least 1400 parts per million (ppm), and (vii) at least one ingredient selected from the group consisting of carnitine, methionine and cysteine, each by weight on a dry matter basis, wherein the composition is fed to a canine or feline.

7. The kit of claim 6 further comprising in separate containers in a single package or in separate containers in a virtual package, as appropriate, at least one of (1) a renal drug, (2) a renal diagnostic device, (3) a means for communicating information about or instructions for admixing a food composition containing protein, sodium, potassium, phosphorous, taurine, EPA and at least one ingredient selected from the group consisting of carnitine, methionine and cystine, and one or more supplements containing sufficient protein, sodium, or potassium to produce a food composition containing relatively low amounts of protein, sodium, and potassium when the supplement(s) are admixed with the food composition containing protein, sodium, potassium, phosphorous, taurine, EPA and least one ingredient selected from the group consisting of carnitine, methionine and cystine, (4) a means for communicating information about or instructions for using a food composition comprising one or more food ingredients containing protein, sodium, potassium, phosphorous, taurine, EPA and least one ingredient selected from the group consisting of carnitine, methionine and cystine for treating kidney disease, (5) a means for communicating information about or instructions for administering in conjunction a food composition comprising one or more food ingredients containing protein, sodium, potassium, phosphorous, taurine, EPA and least one ingredient selected from the group consisting of carnitine, methionine and cystine and a renal drug for treating kidney disease, and (6) a means for communicating information about or instructions for administering in conjunction a food composition comprising one or more food ingredients containing protein, sodium, potassium, phosphorous, taurine, EPA and least one ingredient selected from the group consisting of carnitine, methionine and cystine and using renal diagnostic devices for determining kidney function and evaluating the presence and severity of renal insufficiency or dysfunction.

8. The composition of claim 1, wherein the amount of taurine is about 2100 ppm.

9. The composition of claim 3, wherein the amount of taurine is from about 1400 to about 2100 ppm.

10. The composition of claim 4, wherein the amount of taurine is from about 1400 to about 2100 ppm.

11. The kit of claim 6, wherein the amount of taurine is from about 1400 to about 2100 ppm.

* * * * *